US006773398B2

(12) United States Patent
Ogasawara et al.

(10) Patent No.: US 6,773,398 B2
(45) Date of Patent: Aug. 10, 2004

(54) ULTRASONIC DIAGNOSIS APPARATUS AND OPERATION DEVICE

(75) Inventors: Yoichi Ogasawara, Nasu-Gun (JP); Naohisa Kamiyama, Otawara (JP); Akihiro Sano, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/290,190

(22) Filed: Nov. 8, 2002

(65) Prior Publication Data

US 2003/0135116 A1 Jul. 17, 2003

(30) Foreign Application Priority Data

Nov. 21, 2001 (JP) .................... P2001-356491

(51) Int. Cl.[7] ............................... A61B 8/00
(52) U.S. Cl. ..................... 600/437; 128/922
(58) Field of Search ................ 600/437, 443, 600/447; 128/920–922

(56) References Cited

U.S. PATENT DOCUMENTS

| 5,050,610 A | * | 9/1991 | Oaks et al. ................. 600/437 |
| 6,440,072 B1 | * | 8/2002 | Schuman et al. ........... 600/437 |
| 6,458,081 B1 | | 10/2002 | Matsui et al. |
| 6,475,146 B1 | * | 11/2002 | Freiburger et al. .......... 600/437 |

* cited by examiner

Primary Examiner—Francis J. Jaworski
(74) Attorney, Agent, or Firm—Oblon, Spivak, McClelland, Maier & Neustadt, P.C.

(57) ABSTRACT

An ultrasonic diagnostic apparatus comprises: an operation device which is configured to communicate with a main frame connected to an ultrasonic probe and which an operator of the main frame and the ultrasonic probe may carry and; a system controller to execute a workflow system which switches the operation of the main frame by sequentially executing a plurality of execution items (activities), which is executed by operation of the main frame, according to the work procedure (workflow protocol) predetermining the execution sequence of execution items, and alters the sequence of the execution items in compliance with the operation of the operation device.

20 Claims, 17 Drawing Sheets

ULTRASONIC DIAGNOSIS APPARATUS AND OPERATION DEVICE

BACKGROUND OF THE INVENTION

1. Field of the Invention

The present invention relates to an ultrasonic diagnostic apparatus and its operation device. More particularly, the present invention relates to contrivance of a dedicated suitable input device for a workflow system supporting operation of apparatus during detection or diagnosis.

2. Description of Related Art

Ultrasonic signals have been clinically used in various fields, and one of them is an application to an ultrasonic diagnostic apparatus. The ultrasonic diagnostic apparatus acquires an image signal through transmission and reception of an ultrasonic signal toward and from a subject and is used in a variety of modes utilizing non-Invasiveness of the signal. One typical type of ultrasonic diagnostic apparatus produces tomographic images of a soft tissue of a living body by adopting ultrasonic pulse reflection imaging. This imaging method is noninvasive and produces a tomographic image of the tissue. Compared with other medical modalities such as diagnostic X-ray imaging, X-ray CT imaging, MRI, and diagnostic nuclear medicine imaging, the imaging method has many advantages: real-time display is possible, a compact and relatively inexpensive apparatus can be constructed, patient exposure of X-rays or the like will not occur, and blood imaging is possible thanks to ultrasonic Doppler imaging. The imaging method is therefore most suitable for diagnosis of the heart, abdomen, mammary gland, and urinary organs, and for diagnosis in obstetrics and gynecology. In particular, pulsation of the heart or motion of a fetus can be observed in real time through simple manipulation that in as simple as placing ultrasonic probe on a patient's surface. Moreover, since patient exposure need not be cared about, screening can be carried out many times repeatedly. Furthermore, there is an advantage that an apparatus can be moved to a bedside position for ready screening.

For screening the heart or abdominal organs, contrast echo imaging has newly been introduced and spotlighted, by which an ultrasonic contrast medium is trans-venous injected into a patient for evaluating the kinetics of blood flow. Since trans-venous injection of a contrast medium is less invasive than trans-arterial injection, the method is becoming popular. The main component of the contrast medium is micro-bubbles that act as a source of reflection of ultrasonic waves. The larger the amount and concentration of injected contrast medium is, the larger the effect of contrast imaging is. However, since the bubbles are crushed due to irradiation of ultrasonic waves, the time during which the effect of contrast imaging persists is shortened. Although a contrast medium characteristic of high persistency and high durability against sound pressure has been developed in recent years, the long-term persistence of the contrast medium in a human body predictably raises invasiveness.

Since the life of contrast medium is transitory as described above, examination time of contrast echo imaging is limited. Consequently, compared with an examination without a contrast medium, assistance is necessary for works such as manipulation of the apparatus, preparation and injection of a contrast medium, and control of examination time, which necessitates more manpower. And due to the limited examination time, sequential examination procedure (examination scenario) of contrast echo imaging as a routine examination is fixed, and it is necessary to execute the examination scenario smoothly.

Concerning this issue, proposed is an ultrasonic diagnostic apparatus mounting "workflow system" (also called Intelligent Assistant System: IASSIST) which displays examination procedure in accordance with an examination plan, in order to carry out a menu item included in the displayed examination procedure with one switch action, retrieves small program correspondent with each menu item (also called "activity") and implements this program (ref: Japanese Patent Application KOKAI Publications No.2001-137237).

With the use of the workflow system, examination procedure is guided and switching operation is simplified, so that the efficiency of examination is raised and mistakes of examination are reduced. its effect become remarkable particularly in the examination such as of the contrast echo imaging.

However, in the ultrasonic examination, especially observing dynamic kinetics of blood flow with contrast medium an operator such as a doctor or a technician should hold an ultrasonic probe touched to a subject (patient) in order to maintain the same region of interest, consequently, switching operation to the apparatus under such a circumstance forces the operator to bear the physical burden. In addition, as the operator needs to turn one's gaze on a switch on a control panel (such as a console and an operation panel) to carry out switching operation, the aimed region of interest is often missing and needs adjusting anew. It means a waste of time.

The above described ultrasonic diagnostic apparatus with workflow system surely simplifies a complicated sequential switching operation, but it was not invented in consideration of the above operator's circumstances, it still requires switching operation on the part of the main frame of the apparatus. In regard to this point, it stays unchanged from the conventional one.

SUMMARY OF THE INVENTION

The present invention has been made in view of the described circumstances in the prior art. It is an object of the present invention to provide an ultrasonic diagnostic apparatus and an operation device for optimizing the advantage of the workflow system (also called Protocol Assistant System: PAS, however for the convenience of explanation, hereinafter abbreviated to WFS) so that a doctor or a technician, who operates an ultrasonic diagnostic apparatus while the workflow system is on and scans with an ultrasonic probe, especially may be relieved from the physical and mental stress, concentrate on images and diagnose efficiently.

The above described workflow system has the advantage of guiding an examination procedure, reducing the number of times of switching operation, such as a change-over of modes and a setting of conditions on images, to a few times or one, and proceeding with a series of examination smoothly. By taking this advantage, the operation may be done at hand without reaching out to a control panel installed to the ultrasonic diagnostic apparatus daringly A further object of the present invention is to provide a dedicated input device as a means for improving the function of the workflow system further, especially a small remote control input device with bare essentials of switches necessary to operate the workflow system. The present invention is accomplished based on the above idea.

In order to achieve the foregoing object, as one aspect of the invention, there is provided an ultrasonic diagnostic apparatus comprising: an ultrasonic diagnostic apparatus comprising: a main frame configured to produce an ultrasonic Image using a signal detected by an ultrasonic probe; and an operation device configured to remote-control an operation of the main frame, wherein the operation device comprises a button adopted to specify a function necessary for the operation of the main frame and a processing circuit configured to carry out processing necessary for obtaining the function.

Preferably, the operation device is formed into a portable type or a detachable type of operation device or may be configured to communicate by radio waves with the mainframe.

It is preferred that the ultrasonic diagnostic apparatus further comprises control means configured to switch the operation of the main frame by sequentially executing a plurality of execution items in accordance with the work procedure which predetermines an execution sequence of a plurality of execution items or in addition to the above, further comprises to alter the execution sequence of the execution items in compliance with the operation of the operation device.

It is also preferred the ultrasonic diagnostic apparatus further comprises generating means configured to generate a display image by means of combining at least one of icons and letter strings which are allocated to the plurality of the execution items executed by the control means and ultrasonic image generated from the signals received by the ultrasonic probe.

Further preferably, the operation device comprises execution buttons and shift buttons which give predetermined control commands to the control means by an operation of an operator, the execution means selects at least one of the plurality of the execution items when receiving the control command given by the shift button, and executes at least one of the plurality of the execution items selected by the operation of the shift button when the control command is received, the generating means has changing means for changing the display status of at least one of the icons and the letter strings in order to visually grasp on the display at least one of the execution items selected by the operation of the shift button. Or the operation device further comprises a change-over button switching the operation concerning the work sequence and the operation concerning the main frame each other is configured to communicate by radio waves with the main frame, the control means further comprises the control means for controlling and allocating at least one of switching functions set in the main frame to switches on the operation device so that the switching function may be executed by the operation device.

Still preferably, the buttons are specialized to the selected functions, the selected function is a function to freeze an ultrasonic image, the ultrasonic diagnostic apparatus further comprises a plurality of buttons which are specialized to one of the functions to freeze, printout and store an ultrasonic image, the function of each button is customized to the function frequently used in diagnosis with the ultrasonic diagnostic apparatus, or the function of each button is allowed individually by each operator to be customized, stored, and recalled.

It is also preferred the operation device further comprises a vibration mechanism having a driving circuit which works when a predetermined control command is received, and the control means further comprises communicating means for giving the control command to the operation device so that the vibration mechanism vibrates, or further comprises a loudspeaker outputting voice when a predetermined control command is received, and the control means further comprises communicating means for giving the control command to the operation device so that the loudspeaker outputs voice both in case where at least one of predetermined conditions are met, the predetermined conditions including a change-over of a contrast echo mode set in the ultrasonic diagnostic apparatus, elapsing of an predetermined alarm time, and finding of an unusual electrocardiographic condition of a patient. Or it is still preferred the operation device further comprises a microphone receiving voice including the operator's diagnostic observation, and the control means further comprises recording means for recording the voice when the operator's diagnostic observation is provided.

As another aspect of the present invention, there is an operation device used for the ultrasonic diagnostic apparatus comprising a main frame configured to produce an ultrasonic image using a signal detected by the ultrasonic probe and to be remote-controlled by the operation device, the operation device comprising: a button adopted to specify a function necessary for the operation of the main frame and a processing circuit configured to carry out processing necessary for obtaining the function, Preferably, the operation device further comprises: an LED display indicating both a residual quantity of a battery for power supply and a communication status with the main frame; and the processing circuit executing necessary procedure to distinctively indicate at least one of a lack of the residual quantity of the battery, a waiting status and an established status of the communication, or liquid crystal screen displaying at least a menu and present status of the operation of the operation device; and the processing circuit executing a necessary procedure to display the present status of the operation of the operation device on the screen.

BRIEF DESCRIPTION OF THE DRAWINGS

In the accompanying drawings,

FIG. 2 is an example of display of icon type WFS menu when WFS is on;

FIG. 3 is an example of display of letter string type WFS menu when WFS is on;

FIG. 6 is an example of displayed screen on the monitor when WFS is on;

DETAILED DESCRIPTION OF PREFERRED EMBODIMENTS

Hereinafter, preferred embodiments of the present invention will be described with reference to the accompanying drawings.

(First Embodiment)

Figure 1:
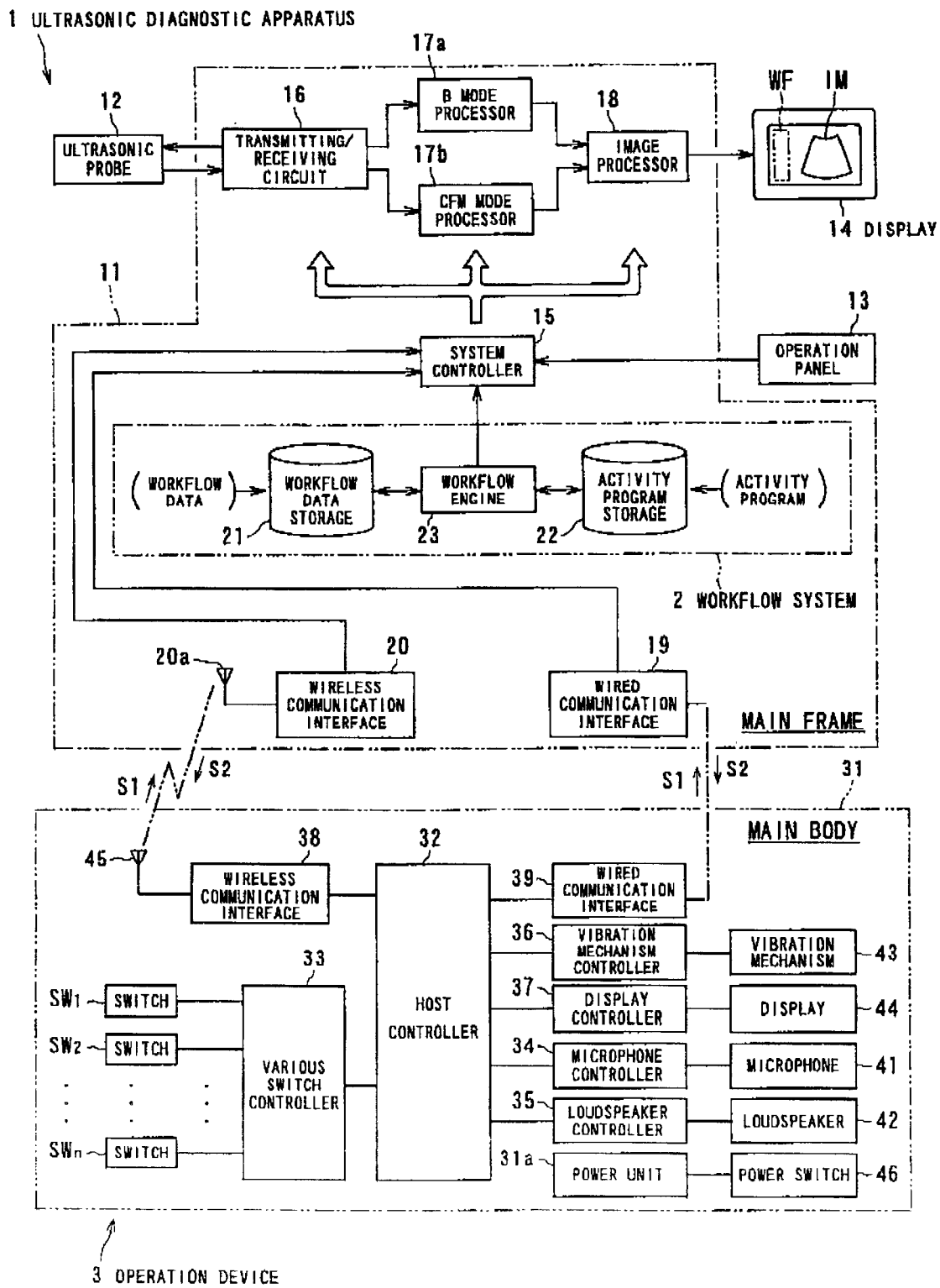
FIG. 1 is a schematic block diagram depicting an overall configuration of an ultrasonic diagnostic apparatus and its operation device according to the first embodiment of the present invention.

A medical imaging diagnostic system shown on FIG. 1 comprises, in addition to an ultrasonic diagnostic apparatus 1 as a modality, a workflow system (WFS) 2 mounted to the ultrasonic diagnostic apparatus 1 and operation device 3 which can operate ultrasonic diagnostic apparatus 1 by remote control.

The hardware of the ultrasonic diagnostic apparatus 1 is configured with, as shown on FIG. 1, a main frame 11, an ultrasonic probe 12, an operation panel 13 and a monitor 14 connected to the main frame 11. The operation panel 13 is equipped with input devices such as switches, buttons, a keyboard, a trackball and a mouse.

The ultrasonic probe 12, which is responsible for transmitting and receiving an ultrasonic signal toward and from a patient, includes piezoelectric transducers made of piezoelectric ceramic or the like as electromechanical bilateral converting elements. For example, a plurality of piezoelectric transducers are set in an array and incorporated in the distal part of the probe, thus constructing the phased array type probe 12. The probe 12 converts driving voltage pulses applied by the main frame 11 into ultrasonic pulses and transmits them in a desired direction in a patient body. On one hand, the probe 12 converts ultrasonic echoes reflected from the patient body into electric signals with corresponding voltages.

The main frame 11 comprises a system controller 15 which is a control center of the whole ultrasonic diagnostic apparatus 1 and each unit which operates under the control of the system controller 15, more specifically, a transmitting/receiving circuit 16, a B-mode processor 17a, a CFM (Color Flow Mapping)-mode processor 17b and an image processing circuit 18. And the main frame 11 mounts communication interface (predetermined communication standard such as USB, IEEE1394 etc.) 19 and wireless communication interface (predetermined communication standard such as infrared data communication (IrDA), radio frequency communication (predetermined communication standard such as bluetooth, IEEE802.11 etc.)) 20 which can communicate with the operation device 3. To the wireless communication interface 20, an antenna section 20a such as infrared window and radio antenna is connected.

The transmitting/receiving circuit 16 transmits driving signals to each piezoelectric transducer of the ultrasonic probe 12 at timing with predetermined delay time given to each transmission channel, based on the control signals from the system controller 15. The driving signals make each piezoelectric transducer of the ultrasonic probe 12 transmit ultrasonic signals to a patient. The ultrasonic signal transmitted in a living body is reflected at an unconformable boundary of acoustic impedance of internal tissues and generates an ultrasonic echo signal which involves components scattered by very small scattering elements in the body. The transmitting/receiving circuit 16 receives the ultrasonic echo signals as echo signal of a corresponding voltage quantity through each piezoelectric transducer of the ultrasonic probe 12, executes delay controlling process and adding process to the echo signal and outputs the processed signal to the next course of both B-mode processor 17a and CFM-mode processor 17b.

The B-mode processor 17a wave-detects an envelope of received signal from the transmitting/receiving circuit 16 and outputs the detected signal, which represents form information of a tissue, to image processing circuit 18. And the CFM-mode processor 17b obtains velocity information from the electrical signal received from the transmitting/receiving circuit 16 by frequency analysis and outputs the measurement result, which represents moving velocity information of blood flow or a tissue, to the image processing circuit 18.

The image processing circuit 18 receives the signals from the B-mode processor 17a and the CFM-mode processor 17b, then generates, superimposes and juxtaposes various images related to B-mode image and CFM image under the control of the system controller 15. Furthermore, it carries out quantitative analysis, measurement and image processing such as adding information which indicates the result of the analysis on the image, finally it converts image signals into a TV scan signal and outputs the signal to a monitor 14. In this manner, as shown on FIG. 1, an ultrasonic image (including various images related to B-mode image and CFM Image and Information Indicating the result of measurement and analysis) IM is displayed on the monitor 14.

The image processing circuit 18 has a function of a means for generating displayed images of the present invention. More precisely, when the WFS 2 is on, under the control of the system controller 15, responding to the command given by the operation panel 13 or the operation device 3, the image processing circuit 18 converts various image signals such as menu, icon, letter string etc. for WFS 2 into a TV scan signal and outputs the signal to a monitor 14. In this manner, as shown on FIG. 1, besides the ultrasonic image IM, as display screen for the sake of the WFS 2, for example, the WFS menu screen M1 including icon or letter string is displayed at the proper position of the monitor 14.

The system controller 15 has a function of a controlling means. One example of the system controller 15 comprises a CPU (processor) connected to an unshown internal bass, a memory (RAM/ROM), a hard disk drive, removable media (CD-ROM, flexible disk, memory card etc.) drive and other peripheral equipment, has a function of a computer, controls an operation of the whole ultrasonic diagnostic apparatus 1 following the procedure programmed in advance at examination. The control operation is concerning each mode such as diagnosis, examination, display etc. or transmitting/receiving condition, and is carried out by the command entered from the operation panel 13 and/or the operation device 3.

The WFS 2 is configured with software which materializes the control means of the present invention through the operation of the system controller 15, an workflow system disclosed by Japanese Patent Application KOKAI Publications No.2001-137237 Is adapted as the software for example. Based on a data (hereinafter called "workflow data") of a work procedure (hereinafter called "workflow protocol") which predetermines execution sequence of a plurality of execution items (hereinafter called "activities") executed by the operation of the main frame 11, the WFS 2 configured to sequentially reads out a small program (hereinafter called "activity program") corresponding to a plurality of activities and executes the program so as to change over an operation of the main frame 11, and the WFS 2 is also configured to change the execution sequence of activities in compliance with the operation of the operation device 3.

The configuration of software module of the WFS 2, as shown on FIG. 1 for example, comprises a workflow data storage 21 which houses workflow data, an activity program storage 22 which houses activity program and a workflow engine 23 which reads out and executes an activity program, corresponding to each activity at each stage of the workflow from the activity program storage 22, based on the workflow data in the workflow data storage 21.

Figure 2:
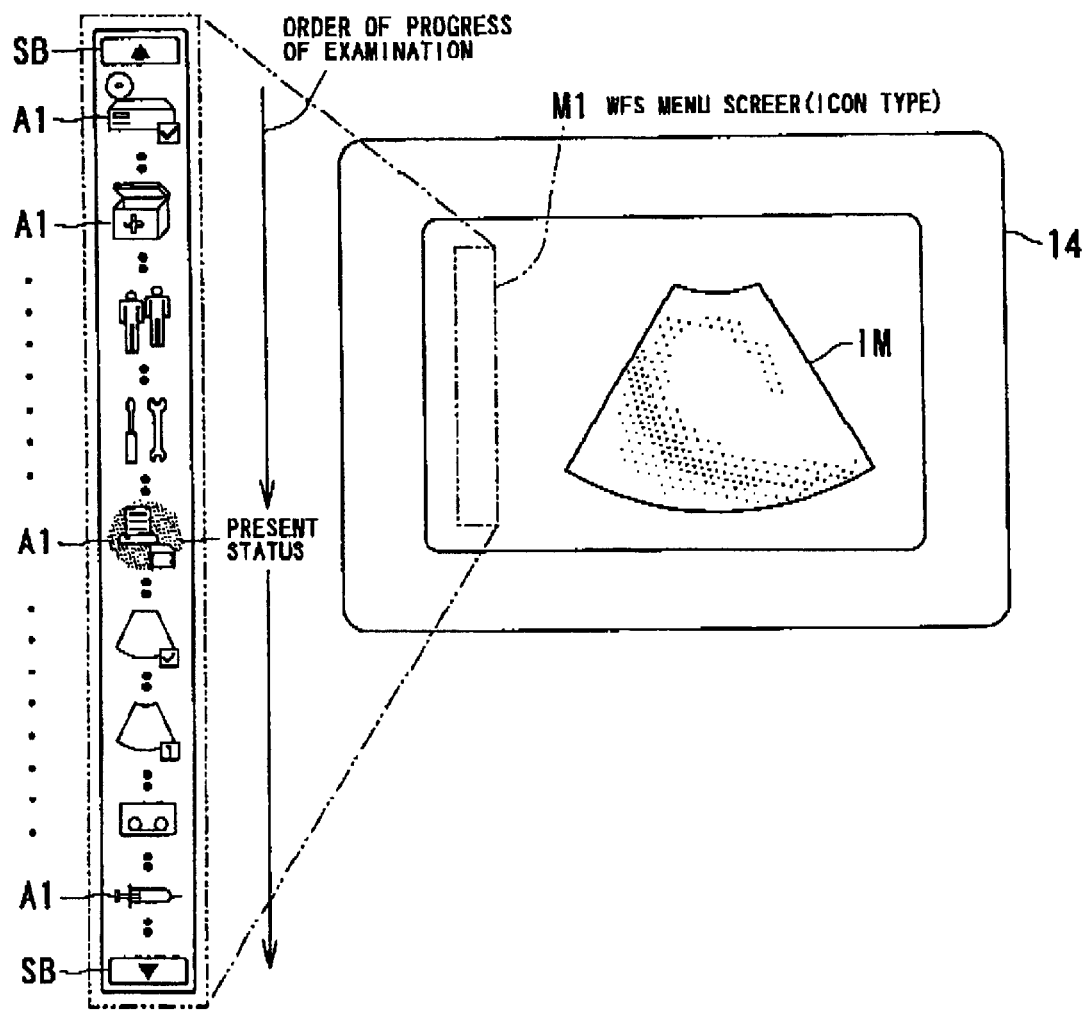
Figure 3:
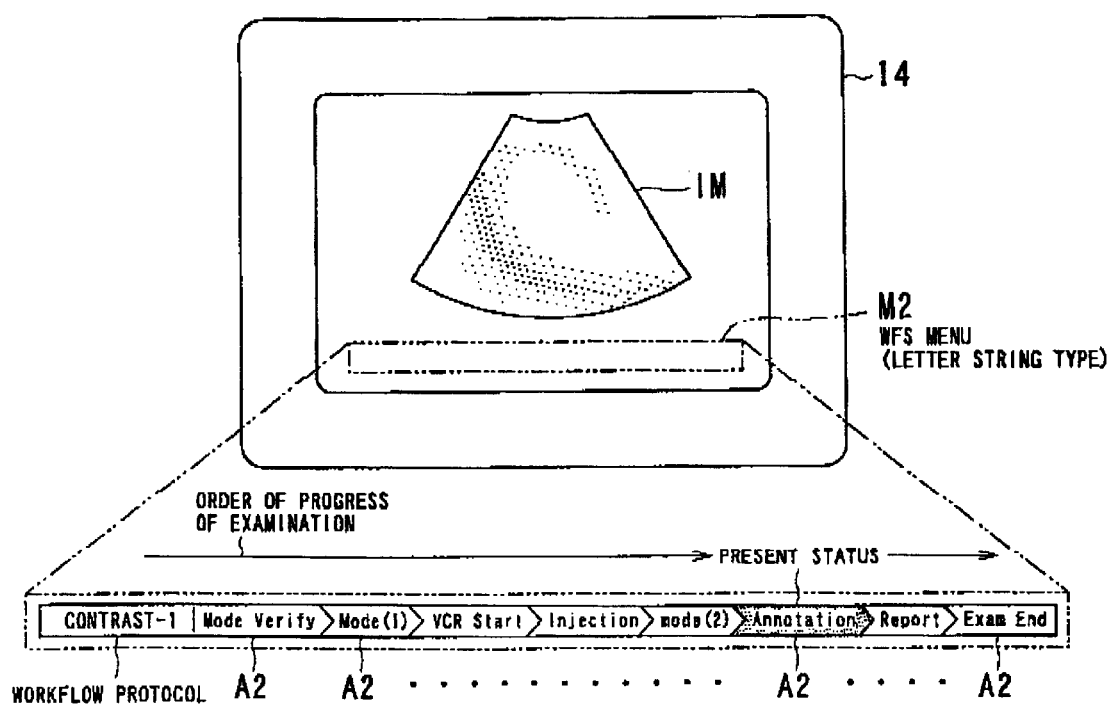

FIG. 2 and FIG. 3 illustrate examples of WFS menu screens which display on the monitor 14 an activity, the execution item of the WFS 2 with the use of an icon A1 whose picture symbolizes the contents of execution (ultrasonic scan, injection of a contrast medium etc.) and an image of letter string A2 respectively. The WFS menu screen is displayed on the monitor 14 by the execution of the WFS program operated by the system controller 15.

For example, FIG. 2 illustrates an icon type menu screen M1, which is displayed longitudinally on the edge of the monitor 14 (left side of the monitor on FIG. 2), concurrently with an ultrasonic image IM at the central part of the monitor 14. The icons A1 . . . A1 for each activity in the WFS menu screen M1 are aligned in the order of the progress of examination from the top of the menu screen M1 in the longitudinal direction to the bottom. Each icon A1 . . . A1 can be scrolled up and down by operating scroll buttons SB, SB located both at the top and the bottom of the WFS menu screen M1. And the icon A1 corresponding to the activity in execution is displayed different from others so as to recognize it is in execution, in the example on FIG. 2, color (background color) is changed appropriately.

FIG. 3 illustrates a letter string type menu screen M2, which is displayed laterally on the edge of the monitor 14 (bottom of the monitor on FIG. 3), concurrently with an ultrasonic image IM at the central part of the monitor 14. The letter strings A2 . . . A2 for each activity in the WFS menu screen M2 are aligned in the order of the progress of examination from the left side of the menu screen M1 in the lateral direction to the right side. For example, the letter string "CONTRAST-1" at the most left side on FIG. 3 indicates a type of workflow protocol (one example of contrast echo examination with a contrast medium in the embodiment). Each letter string A2 . . . A2 can be scrolled side to side by operating unshown scroll buttons in the WFS menu screen M2. And the letter string ("Annotation" in FIG. 3 for example) A2 corresponding to the activity in execution is, as well as the above described icon A1, displayed different from others so as to recognize it is in execution, in the example on FIG. 3I color (background color) is changed appropriately.

The operation device 3 is so configured as to operate the main frame 11 by remote control in communication with the main frame 11, whichever the transmission system is wired or wireless. A communication mechanism and its storage space are required in either case, both wired and wireless systems are adopted as described later in the present embodiment.

In the case of the wired communication system, in order to avoid a contact of electric cable to the floor, it is necessary to prepare a cable suspender or cable storage such as a cable reel. On the contrary, the wireless communication system is superior to the wired one in terms of mobility and handling because; 1) A cable is not caught on by peripheral equipment or instillation fulcrums while operator moves with the operation device 3, 2) A cable does not touch to a patient, therefore, the patient does not feel uncomfortable, 3) A cable preferably does not touch to the floor preferably from the aspect of the sanitation.

As long as the operation device 3 has an appropriate shape and size such as an operator holds on hand and can operate at the place like a bedside of a patient away from the main frame 11, either a portable type (palm size) which is small in size and easy to hold in hand, a console type (not larger than a letter size) which can be put level at the bedside in a examination room, a stationary type and so on may be applicable, the selection of type is according to a preference of a doctor or a technician. In addition, the operation device 3 may be detachable from the main frame 11.

The example of the operation device 3 shown on FIG. 1 interiorly comprises each unit, namely a host controller 32 such as CPU the control center, various controllers and interfaces connected to the host controller 32, in other words, various switch controllers 33, a microphone controller 34, a loudspeaker controller 35, a vibration mechanism controller 36 (driving circuit for motor etc.), a display controller 37, a wireless communication interface (predetermined communication standard such as infrared data communication (IrDA), radio frequency communication (bluetooth, IEE802.11 etc.)) 38 and wired communication interface (predetermined communication standard such as USB, IEEE1394 etc.) 39. These units are powered by a power supply unit 31a such as battery which is activated when switch 46 is turned on.

Also mounted to the operation device 3 are a plurality of switches SW1, SW2, . . . , SWn whose functions are changeably alocated, connected to the host controller 32 through the intermediary of various controllers 33 through 37 and the interface 38, a microphone 41 for receiving voice of a doctor's diagnostic observation, a loudspeaker 42 for voice output, a vibration mechanism 43 such as vibrator, a display 44 such as various indicators (LED) and an antenna section 45 such as infrared window or wireless antenna.

The host controller 32 is configured with, for example, an IC (Integrated Circuit) unit such as mouse controller having CPU on board, or may be configured with an IC unit integrated with at least one of other controllers 33 through 37, interfaces 38 and 39.

While the host controller 32 transmits control command S1, such as various switch commands set-up beforehand, to the main frame 11 in response to the operation by an operator through the intermediary of the wireless communication interface 38 or the wired communication interface 39, the host controller 32 receives various control commands S2 such as an alarm described later from the system controller 15 of the main frame 11 through the intermediary of the wireless communication interface 38 or the wired communication interface 39, and controls the operation of the ultrasonic diagnostic apparatus 1 by the transmission and reception of the commands.

For the plurality of switches SW1 through SWn, either type of switches such as pushbutton or rotary dial (such as rotary encoder) is applicable. For example, these switches are configured with optical sensing means, so that concavity, convexity and actuators on the surface of the operation device are disposed of and cleaning of the surface becomes easier, or a stain proof cover may be laid over by taking advantage of unrelieved surface consequently.

To the above described switches SW1 through SWn, various switches necessary to operate the WFS 2 are allocated, such as a shift button, an execution button and a changing-over button, and a spare switch. One example of the operation device 3 is shown on FIG. 4 (a front view) and on FIG. 5 (a side view).

Figure 4:
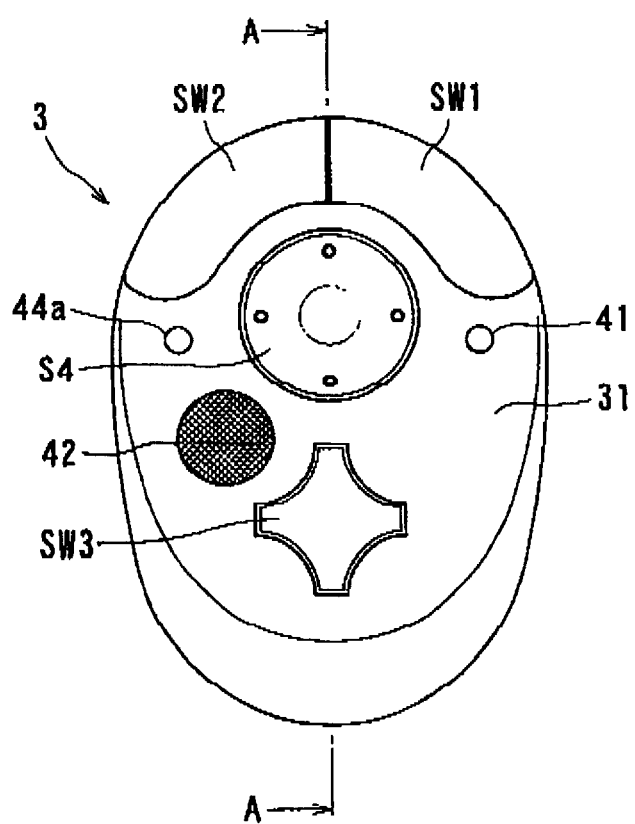
FIG. 4 is a schematic front view of an operation device according to the first embodiment of the present invention.
Figure 5:
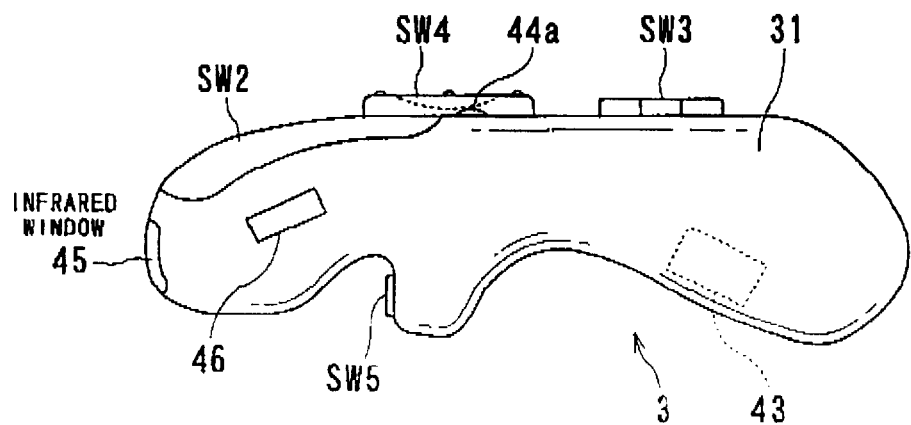
FIG. 5 is a schematic side view of the operation device shown on FIG. 4 from the viewpoint of A—A line.

FIG. 4 and FIG. 5 show an example of the operation device 3 of a portable type. The operation device 3 of the example is made up of a main body 31 with elliptical (ovoid) shape, four switches S1 through SW4 are prepared on the flat surface of the front and one switch S5 on the indented surface of the back, on which a convex portion at center and two concave portions at both side of the convex portion are formed in accordance with the shape of a gripped hand for comfortable holding. And the antenna section 45 is prepared to the side face of the upper part of the operation device 3 in the example, however, in case that the radio frequency communication such as the bluetooth and IEEE 802.11 is adapted and integrated with the host controller 32, it is not necessary to design an independent antenna section.

Figure 6:
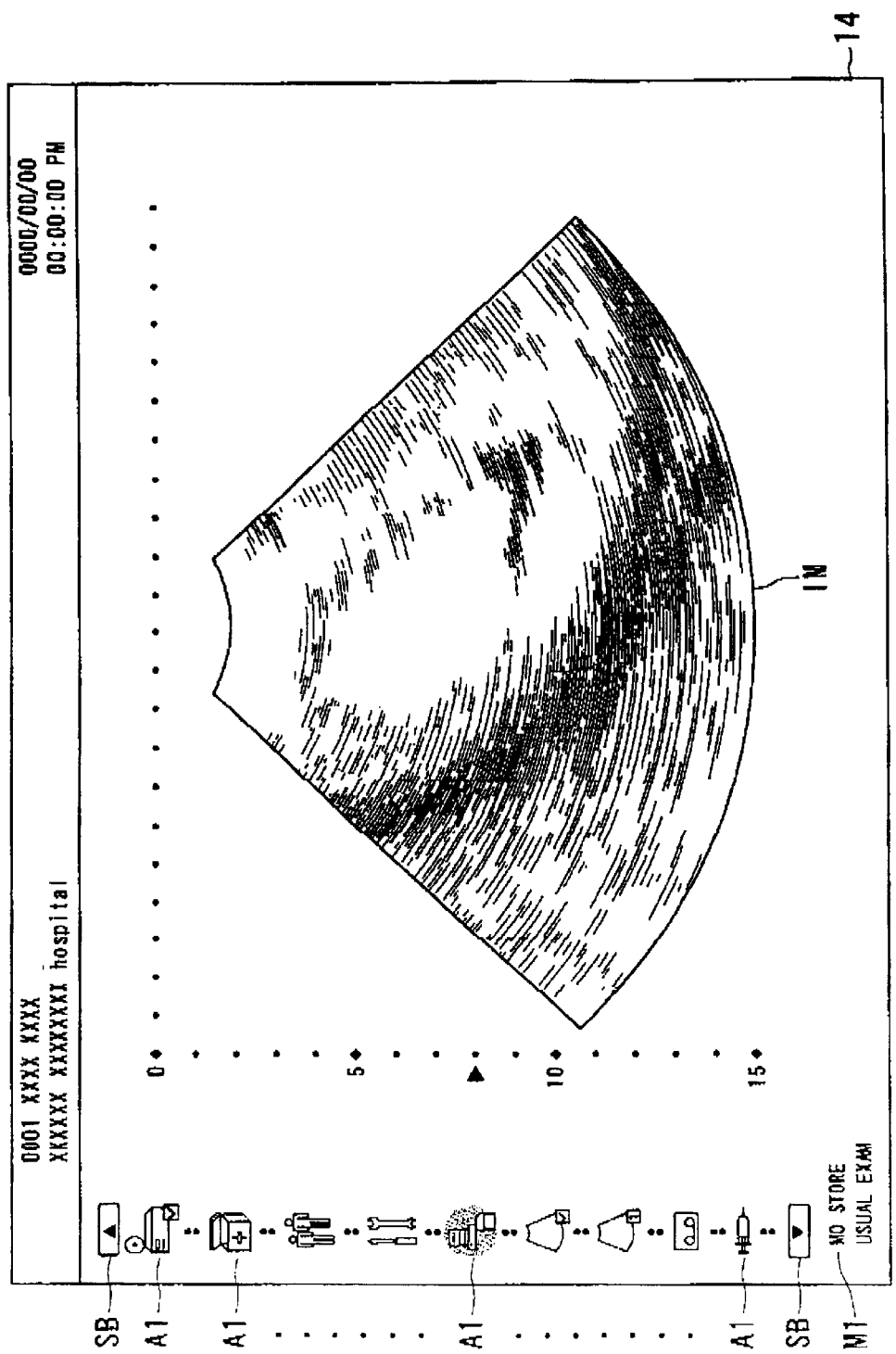
Figure 7:
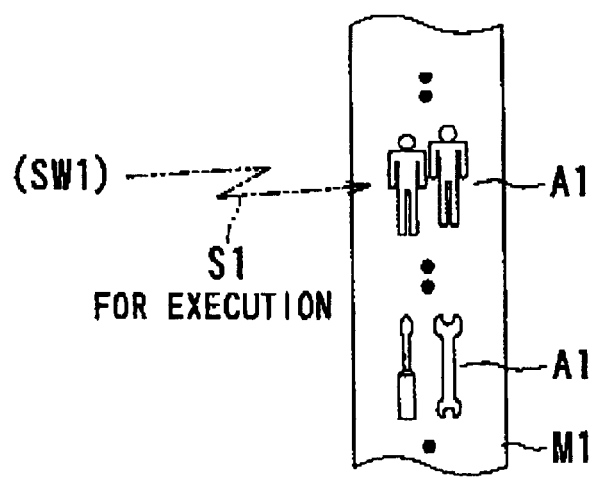
FIG. 7 is a view illustrating the determination of an activity on icon type WFS menu by operating the switch SW1 (execution button) of the operation device.
Figure 8:
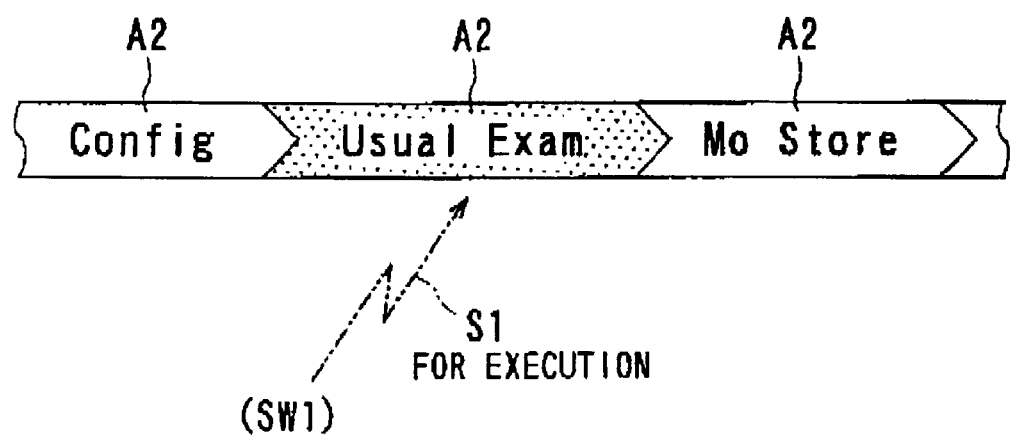
FIG. 8 is a view illustrating the determination of an activity on letter string type WFS menu by operating the switch SW1 of the operation device.
Figure 9:
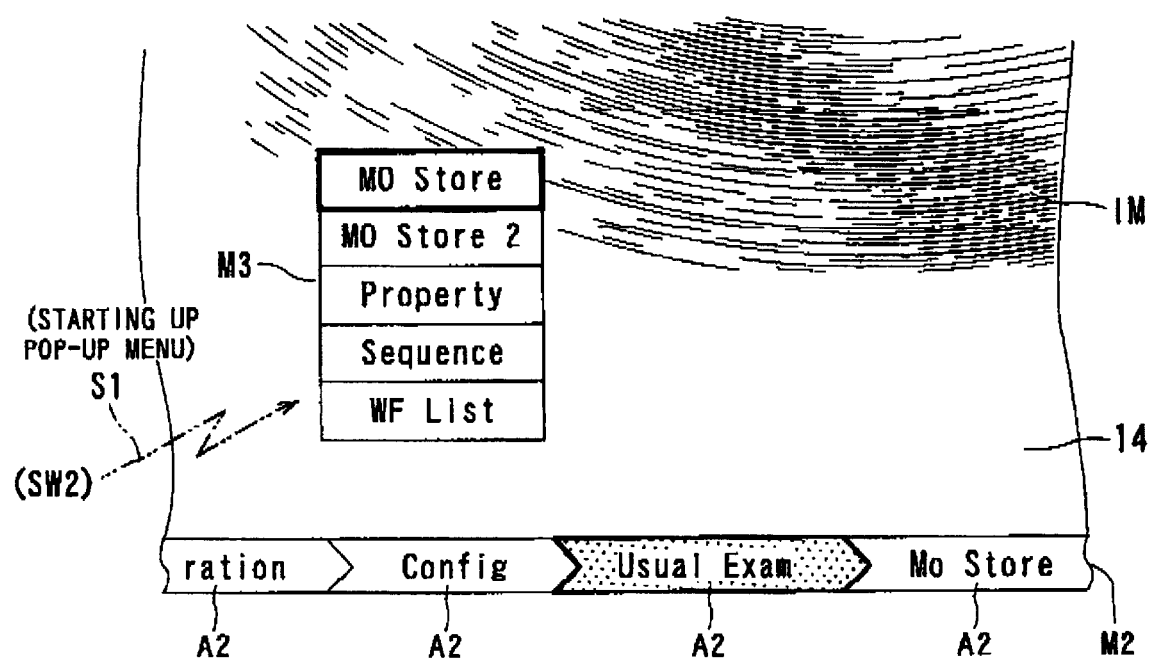
FIG. 9 is a view illustrating the activation of a pop-up menu by operating the switch SW2 (execution button) of the operation device.

FIG. 7 through FIG. 12 illustrate functions executed by the switches SW1 through SW4 when the WFS menu M1 or M2 as shown on FIG. 6 is displayed together with the ultrasonic image IM on the monitor 14 and the WFS 2 is on.

The switch SW1 at the upper right of the front, as shown on FIG. 4, is a push type execution button. In compliance with the control command (switch command) S1 of the switch SW1, one activity is determined by selecting an icon A1 in case that the icon type WFS menu M1 is displayed on the monitor 14 as shown on FIG. 7, or by selecting one letter string A2 in case that the letter string type WFS menu M2 is displayed on the monitor 14 as shown on FIG. 8. The WFS 2 reads out a corresponding program for the execution, or determines other menu In this manner.

The switch SW2 at the upper left of the front, as shown on FIG. 4, is also a push type execution button. As shown on FIG. 9, in case that the letter string type WFS menu M2 is displayed on the monitor 14, in compliance with the control command (switch command) S1 of the switch SW2, a versatile pop-up menu including forced termination, calling out of another scenario is activated and displayed at the appropriate position, apart from the WFS menu M2. The pop-up menu may be activated when the WFS 2 is off.

The switch SW3 at the lower portion of the front, as shown on FIG. 4, is a directional key for shifting position longitudinally and laterally. In compliance with the control command (switch command) S1 of the switch SW3, one of the activities is selected by pointing up a corresponding icon A1 in case that the icon type WFS menu M1 is displayed on the monitor 14 as shown on FIG. 10, or by pointing up a corresponding letter string A2 in case that the letter string type WFS menu M2 is displayed on the monitor 14 as shown on FIG. 8.

The switch SW4 at the center of the front, as shown on FIG. 4, is a directional key with a trackball function for shifting cursor etc. In compliance with the control command (switch command) S1 of the switch SW4, two dimensional positioning, such as an item selection among the activities in the letter string type WFS menu M2 as shown on FIG. 12 and an item selection by a cursor Cl in a measurement menu M4, becomes possible.

The switch SW5 at the back as shown on FIG. 5 is a push type change-over switch, makes it possible to divert another switch from a WFS key to a hardware key used in normal examination so as to change an allocated function of the Intended switch to frequently used function such as "freeze" and "printout". The set-up of the change-over switch may be designed to activate WFS key when the switch SW5 is pressed simultaneously with the intended switch, or to the contrary, to activate a key for normal examination. Or again, the set-up may be designed to activate the WFS key and a key for normal examination alternatively whenever the SW5 is pressed.

Furthermore, the set-up may be designed to make a function of the intended switch changeable according to the activity in execution. For example, a function of "freeze" Is given to the switch SW2 when the mode is changed over to B/W mode. For another example, in case that "REPORT" activity is executed and report screen is displayed, the set-up may be designed to give "PLAY" function to the top of the switch SW3 and "STOP", "REWIND" and "FORWARD" to the bottom, left and right of the switch SW3 respectively.

In addition, among the switches SW1 through SWn, for example, a dedicated switch for instructing microphone 41 to record is included When one of the above described switches SW1 through SWn is operated under the control of the host controller 32 and various switch controllers 33, control command S1 of switch command (any command may be defined) depending on the variety, such as shift button, execution button, change-over button allocated to the intended switch among switches SW1 through SWn is transmitted from the operation device 3 to the main frame 11 by way of the wireless communication interface 38 or the wired communication interface 38

Consequently, the system controller 15 in the main frame 11 may change the operation of the WFS 2 in accordance with control command from the operation device 3

For example, when the system controller 15 receives a control command S1 issued by the operation of a shift button during the execution of the WFS 2, the system controller 15 selects an icon or a letter string representing a certain activity on the monitor 14, or when receiving a control command S1 issued by the operation of an execution button, it reads out and executes a corresponding activity program to an activity selected by the operation of the shift button.

Simultaneously, the image processor 18 alters the display to visually grasp the activity selected by the operation of the shift button through the icon or the letter string on the monitor 14, such as changing color and blinking.

The display 44 is made up of a unicolor or bicolor LED 44a. The display controller 37 receives information of residual quantity of a battery from the power unit 31a and information of communication condition with the main frame 11 from the communication interface 39, then indicates the status on the LED 44a.

A bicolor LED 44a, at the beginning when the power unit 31a is turned on by the operation of the power switch 46, blinks in red color in order to urge an operator to charge a battery in case that the residual quantity is lower than a predetermined quantity. In case that residual quantity of the battery is enough for operation, the LED 44a blinks in green to indicate that the battery is OK and the operation device 3 is in course of establishing communication with the main frame 11. Then, when the communication is established, the blinking in green changes to the lighting in green to indicate that the operation device is ready to use. When the residual quantity of the battery gets low during use, the LED 44a gives the operator a warning by changing status from lighting in green to blinking in red even it communication is established. It is because reliability of continuing use may not be guaranteed.

On the other hand, a unicolor LED 44a, at the beginning when the power unit 31a is turned on, blinks slowly (two times per second, for example) in order to urge an operator to charge a battery in case that the residual quantity is lower than a predetermined quantity. In case that residual quantity of the battery is enough for operation, the LED 44a blinks quickly (four times per second, for example) to indicate that the battery is OK and the operation device 3 is in course of establishing communication with the main frame 11. Then, when the communication is established, the quick blinking changes to the lighting to indicate that the operation device 3 is ready. When the residual quantity of the battery gets low during use, the LED 44a gives the operator a warning by changing status from lighting to slow blinking similar to the bicolor LED 44a.

Voice signals including at least a doctor's diagnostic observation is received by the microphone 41 in order to record the signals through it. In case that the dedicated recording switch previously described is equipped concomitantly, the voice received by the microphone 41 is recorded while the recording switch is pressed, and the display 44 (such as LED) is illuminated to indicate on recording all the while. The recording is stopped by releasing the recording switch, and illumination on the display is put off.

The voice signal received by the microphone 41 is automatically recorded in the report data as voice data or character data to which the voice data is converted by unshown voice recognition/character conversion function after the voice recognition is made.

And the voice signal received by the microphone 41 may be voice-recognized and used as a command for controlling the ultrasonic diagnostic apparatus 11. For example, since the WFS 2 makes an examination progress automatically so long as a corresponding icon or image of letter string of an Intended activity is selected from the WFS menu on the monitor 14 while the WFS 2 is in execution, the operation may be controlled with only simple and relatively small quantity of commands such as "Next" for making the WFS menu go forward, "Back" for backward to the contrary, "OK" for decision, so that the problem of voice recognition probability is almost cleared and reliable control is possible.

The loudspeaker 42, working together with an alarm function of the ultrasonic diagnostic apparatus 11 and in compliance with the control command S2 from the ultrasonic diagnostic apparatus 11, can announce the fact when it is necessary to raise an alarm, such as something is wrong with an electrocardiographic condition of a patient, or when the mode of the contrast echo examination is changed over.

Similar to the above loudspeaker 42, the vibration mechanism 43, working together with an alarm function of the ultrasonic diagnostic apparatus 11 and in compliance with the control command S2 from the ultrasonic diagnostic apparatus 11, vibrates and announces the fact to an operator of the operation device 3 when it is necessary to raise an alarm, such as something is wrong with an electrocardiographic condition of a patient, or when the mode of the contrast echo examination is changed over.

The above voice from the loudspeaker 42 and vibration by the vibration mechanism 43 give the alarm to an operator, such as a doctor or a technician. The alarm function is especially useful when a doctor or a technician desires to take action other than the examination plan prescribes, such as when the operator desires to execute an examination of other mode meanwhile controlling time, when the operator desires to know whether a predetermined time has elapsed or not in consideration of the throughput, or when something is wrong with an electrocardiographic condition of a patient.

For example, at the contrast echo examination, time management is necessary each time phase, which is classified and named by the elapsed time after the injection of a contrast medium, such as arterial phase, arterial-pylic phase and perfusion phase in case of the abdomen, Ordinarily, clock-timer displayed on the monitor 14 is drawn upon, however, it is often the case that executing examination is difficult meanwhile controlling time since the operator concentrates on maintenance of scanning section or on screen. Therefore, manpower for time management is acquired beforehand in some sites.

The operation device 3, working together with a clock-timer function, delivers timing information each predetermined elapsed time after the injection of the contrast medium by alarm sound, voice guide or vibration, so that the above described manpower may be reduced. And the operation device 3 informs the operator of the progress status with voice guide, so that the WFS 2 progresses smoother. Furthermore, warning information may be delivered. The followings may be cited as examples of the voice guide; 1) "Contrast medium is injected", "The mode is changed" for progress contents, 2) "30 second (after the injection of contrast medium)", "4 minutes 30 second (after the injection of contrast medium)" for time management, 3) "MO (magneto-optic disc) is not set" for warning.

Therefore, According to this embodiment, the operation device as a dedicated small remote-control device makes the operationability, which is the advantage of the WFS, simpler and easier. In addition, since the operation device is handy and needs only a few switching operation, a doctor or a technician may operate it without watching it in hand, or while observing the screen, the operator may bring it in sight of the screen to watch, it necessary. So that, the operator may keep the posture to concentrate on a diagnosis without stress and may carry forward the examination (Second Embodiment)

Figure 13:
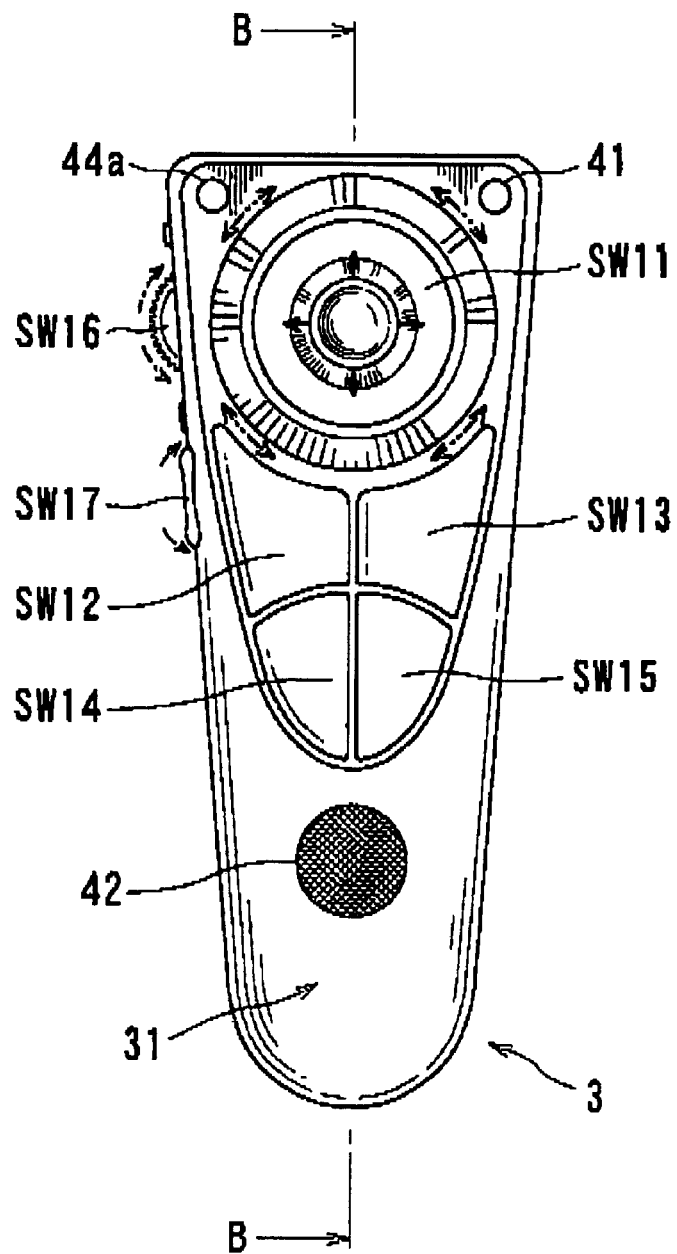
FIG. 13 is a schematic front view of an operation device according to the second embodiment of the present invention.
Figure 14:
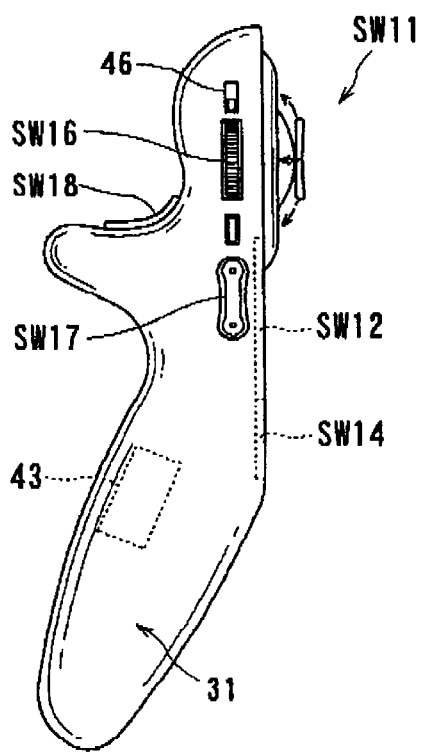
FIG. 14 is a schematic side view of the operation device shown on FIG. 13 from the viewpoint of B—B line.
Figure 15:
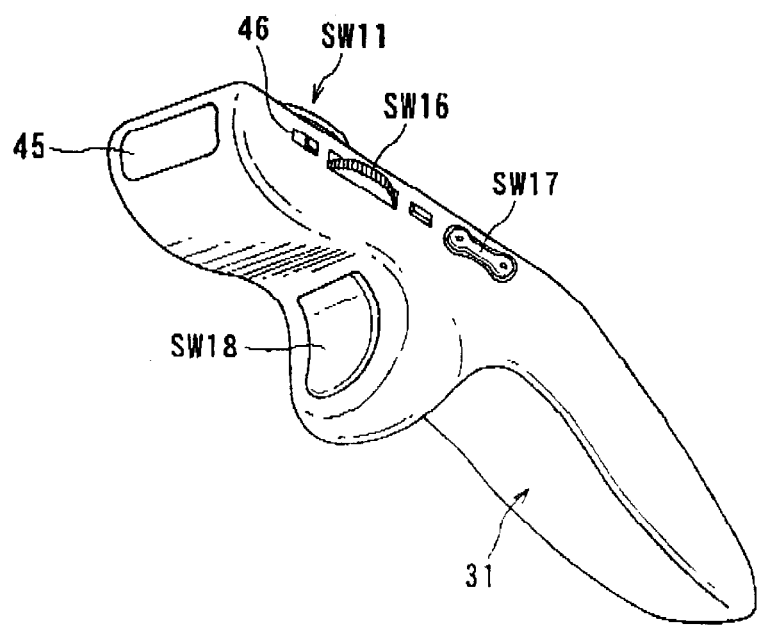
FIG. 15 is an oblique perspective view of the operation device shown on FIG. 13.

Referring to FIG. 13 through FIG. 15, an ultrasonic diagnostic apparatus and an operation device according to a second embodiment of the present invention will be described.

FIG. 13 through FIG. 15 show another example of the operation device 3 pf a portable type. The operation device 3 of the example is made up of a main body 31 with rectangular shape, five switches SW11 through SW15 are prepared on the flat surface of the front and two switches SW16 and SW17 on the left side surface, and one switch SW 18 on the back surface, on which a convex portion at center and two concave portions at both side of the convex portion are formed in accordance with the shape of a gripped hand for comfortable holding.

Among them, the switch SW11 at the upper portion of the front of the device has a combined function of the switches SW1, SW3 and SW4 of the previously described embodiment and comprises a push type execution button to determine an item such as an activity, a directional key to select an item such as an activity by shifting position longitudinally and laterally, a directional key with a trackball function to locate two dimensionally a cursor etc., and a gain control switch utilizing a function of rotary encoder.

The switch SW12 at the middle left of the front, as shown on FIG. 13, is an execution button to activate a pop-up menu similar to the switch SW2 of the previous embodiment.

The switch SW13 at the middle right of the front is a push type execution button to "freeze" a screen, which is not set up in the previous embodiment. Since doctors freeze a screen frequently in course of an examination, for example, when characteristic or interesting image is displayed on the monitor, as occasion may demand, it is very difficult or almost impossible to put "freeze" activity into the sequence of the WFS 2. Therefore, it is very convenient to have a specific button for an independent and frequently taken activity and it improves the operationability of the WFS 2 exceedingly.

The switch SW14 at the lower left of the front is a push type execution button to "printout" an ultrasonic image, which is not set up in the previous embodiment either. Since doctors desire to observe the still Image obtained by freezing the screen, the "printout" activity usually accompanies the above described "freeze" activity, therefore, it is very convenient to have a specific button for an activity accompanying an independent and frequently taken activity, and it improves the operationability of the WFS 2 exceedingly.

And the switch SW15 at the lower right of the front, which is not set up in the previous embodiment either, is also a push type execution button to "save" an ultrasonic image obtained by an ultrasonic scan. Since doctors desire to record interesting images and the "save" activity also accompanies the above described "freeze" activity, it is very convenient to have a fixed button for an activity accompanying an independent and frequently taken activity, and it improves the operationability of the WFS 2 exceedingly.

The switch SW16 at the upper portion of the left side surface, which is not set up in the previous embodiment either, is a rotary type button for adjusting a depth of visual field of an ultrasonic image obtained by an ultrasonic scan.

The switch SW17 at the lower portion of the left side surface, which is not set up in the previous embodiment either, is a push type, button for adjusting a focus of an ultrasonic scan.

And the switch SW18 on the back surface is a change-over switch from the WFS key to a key for normal examination and the other way around.

In addition to the above switches SW11 through SW18, a communication window 45, display 44 and power switch 46 are mounted.

(Third Embodiment)

Figure 16:
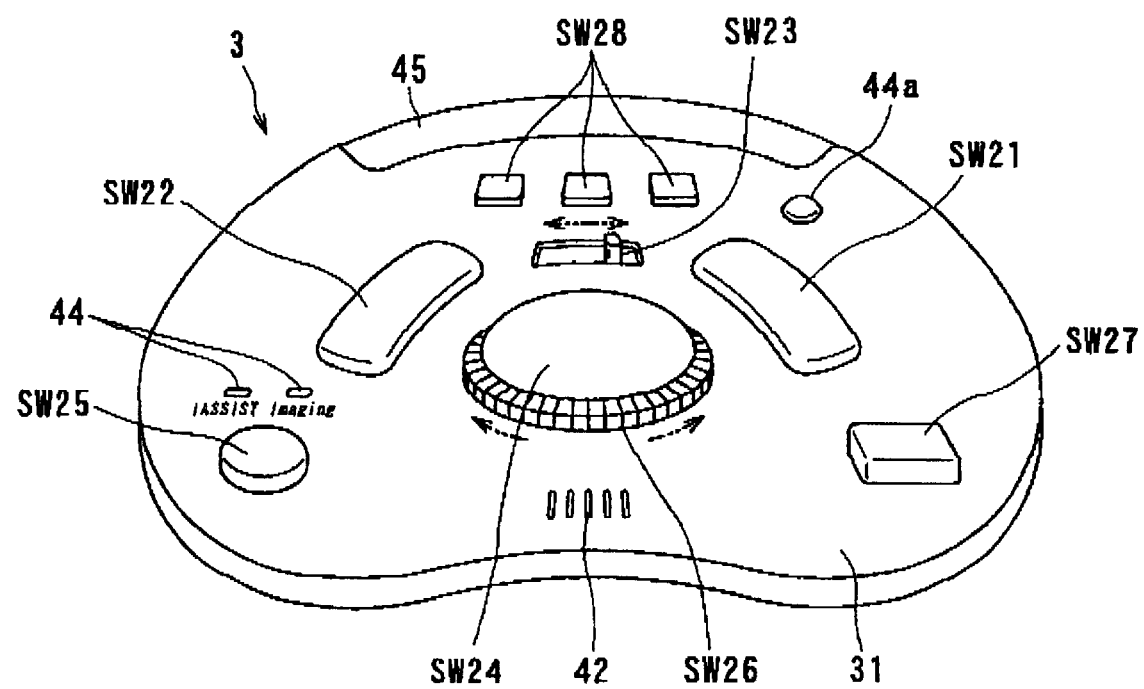
FIG. 16 is a schematic front view of a stationary type operation device according to the third embodiment of the present invention.

Referring to FIG. 16, an ultrasonic diagnostic apparatus and an operation device according to a third embodiment of the present invention will be described.

FIG. 16 shows an example of the operation device 3 of a stationary type. The operation device 3 of the example is made up of a main body 31 with elliptically rounded shape. Prepared to the operation device 3 are an unshown antenna section (communication window) 45 at the side surface of the upper portion, a loudspeaker 42 at the lower portion of the front, a display (indicator) 44 displaying change-over position ("IASSIST" for the WFS in execution and "Imaging" for normal examination on FIG. 16), and various switches SW21 through 29 similar to the previous embodiments.

The switch SW21 at the middle left of the front is an execution button to determine menu etc. with the same function as the switch SW1 of the previous embodiment, the switch SW22 is a push type execution button to activate a pop-up menu as same as the switch SW2 of the previous embodiment, the switch SW23 at the middle right is a directional key for shifting the WFS menu longitudinally or laterally as same as the previous switch SW3, the switch SW24 at the very center of the front is a directional key with a trackball function to shift cursor etc. as same as the previous switch SW4, and the switch SW25 at the left of the front is a change-over switch from the WFS key to the normal operation key as same as the previous switch SW5.

Furthermore, the switch SW26 at the center of the front is a rotary switch for gain control, the switch SW27 at the lower right of the front is a push type switch to "freeze" and the switch SW28 at the upper center of the front is a push type shortcut switch as a custom button to which desired activity or menu may be allocated.

In addition to the above switches SW21 through SW28, a display (LED) 44a is allocated to an appropriate and easily viewable position, for example, at upper right of the front, as shown on FIG. 16.

(Fourth Embodiment)

Figure 17:
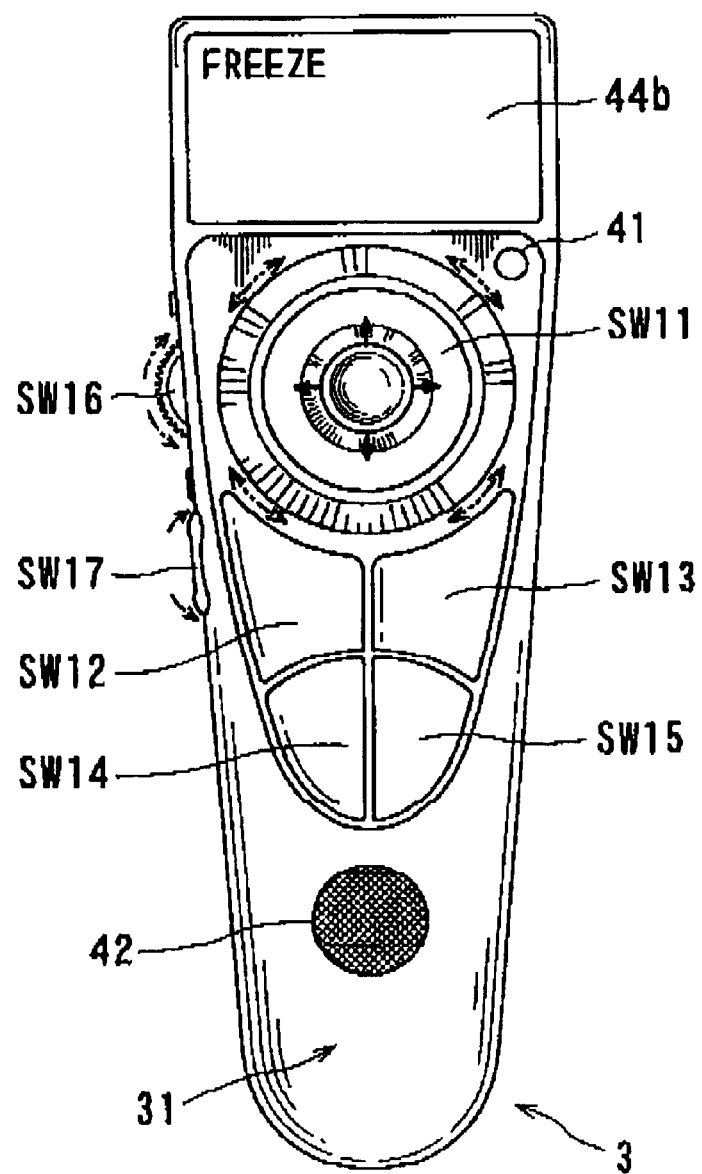
FIG. 17 shows a modified example of the operation device previously described in the second embodiment according to the fourth embodiment of the present invention.

Referring to FIG. 17, an ultrasonic diagnostic apparatus and an operation device according to a fourth embodiment of the present invention will be described.

FIG. 17 shows a modified example of the operation device 3 previously described in the second embodiment. The operation device 3 of the example has a liquid crystal display 44b at the top of the front in lieu of LED 44a of the operation device 3 in the second embodiment as display 44. Since the other components or the configuration are as same as the operation device 3 of the second embodiment and have been already described, description will be omitted.

By giving a liquid crystal display 44b to the operation device 3 like a cellular telephone, and by making the operation device 3 display a menu, command and/or alarm in lettering, it becomes easier to grasp an appropriate perception of the present status of the operation device 3, for example, in a status of controlling the WFS or of controlling directly the main frame 11 for normal examination.

In addition to the above, it may be possible to upgrade the representational function, such as by changing color of the background of liquid crystal display. For example, when the color of the background is green, it indicates that the operation is in a status of controlling the WFS, however, no sooner the status is changed over to controlling directly the main frame 11 than the color of the background changes to red, so that it becomes easier moreover to grasp an appropriate perception of the present status of device operation.

(Fifth Embodiment)

Figure 18:
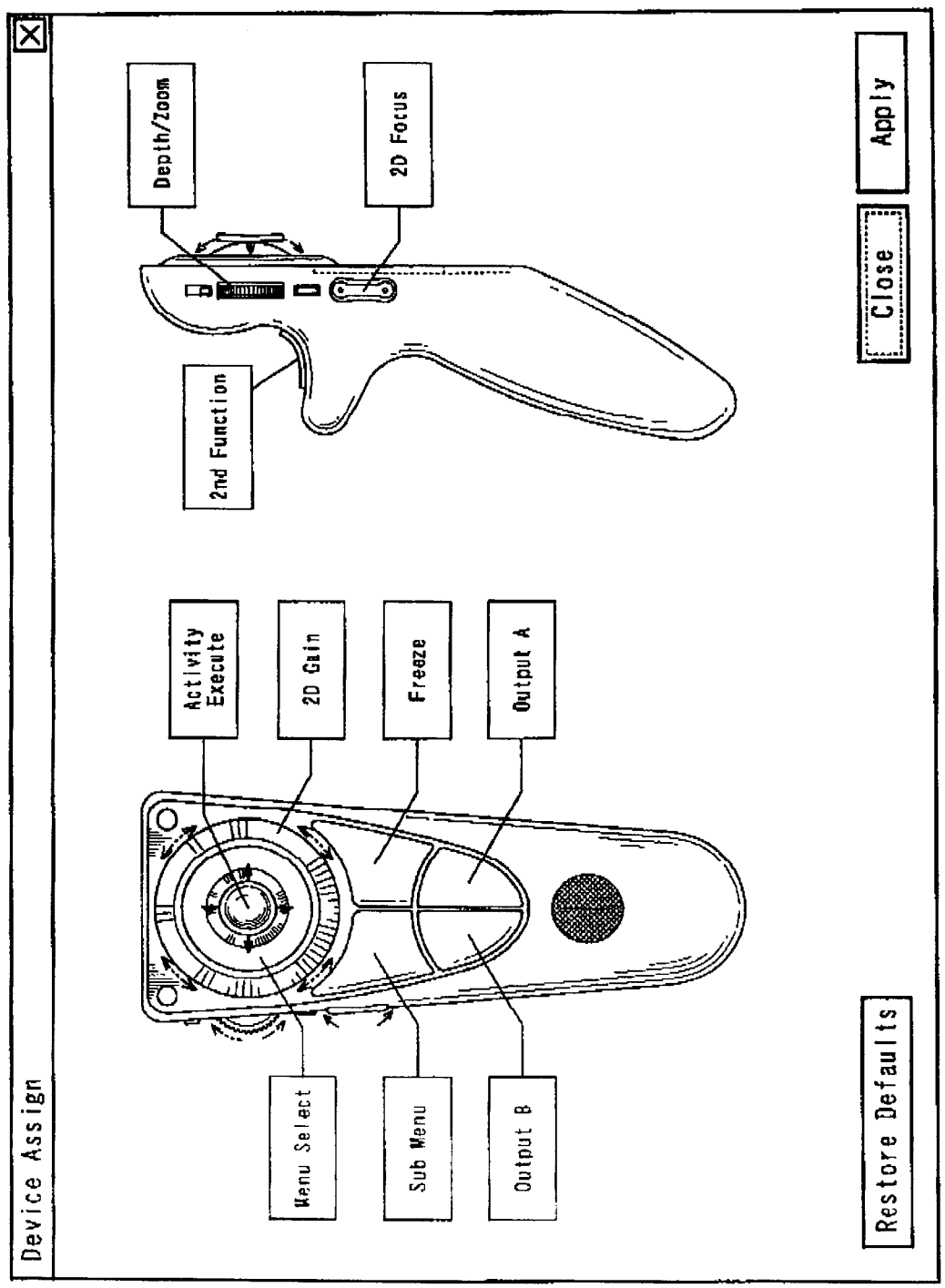
FIG. 18 and FIG. 19 illustrates examples of screen on the monitor displaying the customization of buttons of the operation device according to the fifth embodiment of the present invention.
Figure 19:
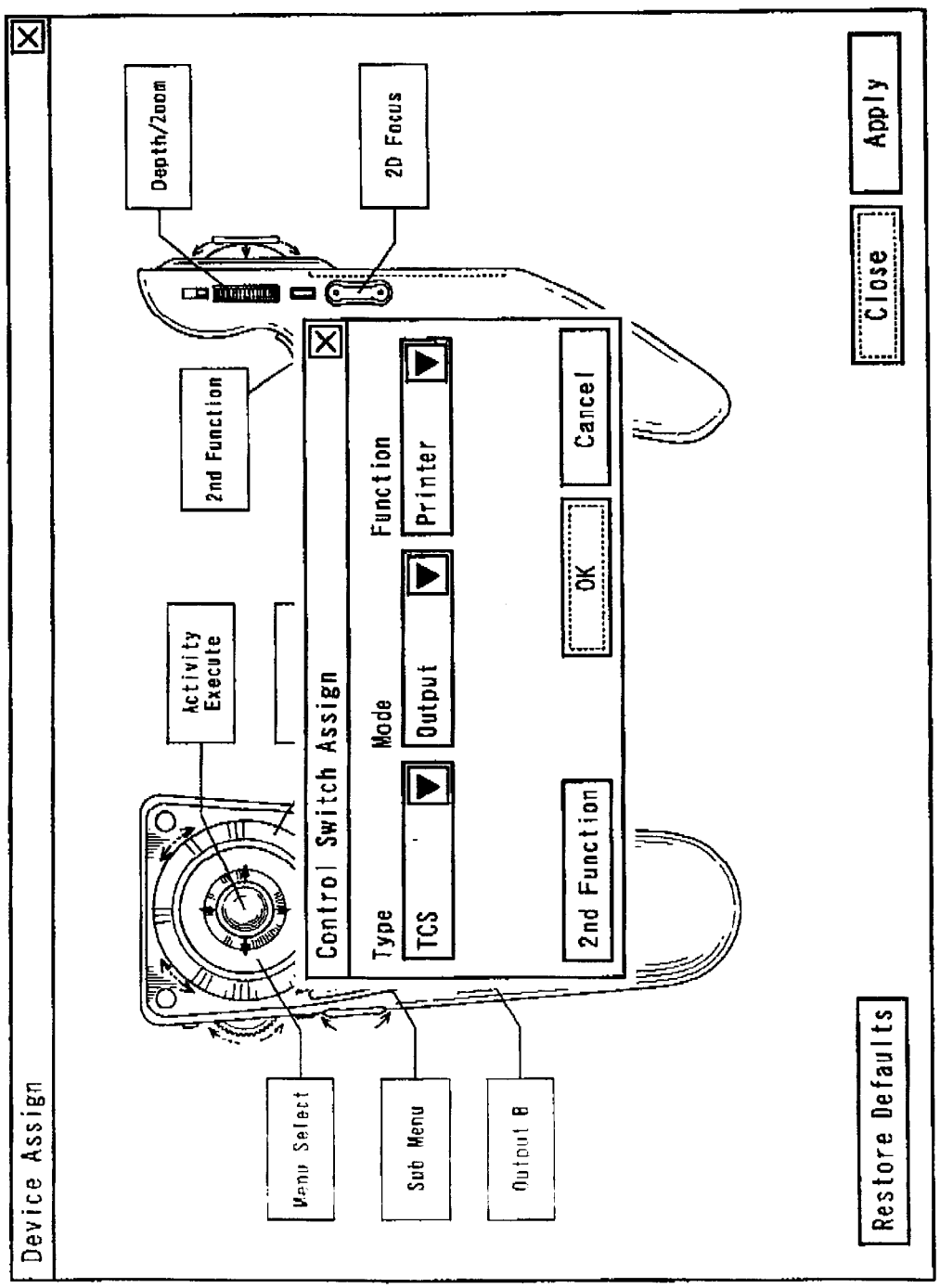

Referring to FIG. 18 and FIG. 19, an ultrasonic diagnostic apparatus and an operation device according to a fifth embodiment of the present invention will be described.

In the fifth embodiment, the operation device 3 is configured with an interface to change over a function of each button, in other words, function of each switch for normal examination may be defined by a user so that a user may freely allocates a function which is frequently used in the ultrasonic diagnosis to a certain button.

Each doctor has one's own way of the examination, and frequently used function of the ultrasonic diagnostic apparatus is different each other. Therefore, it is convenient for a user to customize a function of each switch in accordance with the frequency in use of each person. Since each button may be customized independently from others, each button may be allocated for each operator's exclusive use, and each operator customizes one's own button, so that a plurality of operators may share one operation device 3 customized according to one's preference and each person may control the main frame 11 easier without controlling the WFS 2.

FIG. 18 illustrates an example of a screen on the monitor displaying both the front and one side of the operation device 3 with a name of function allocated to each switch. When a user clicks the name of the function on the screen in order to change the function of some switch, a second window appears. The new window has pull-down menus in which range of choice of type, mode and function are listed, the user may choose one among them of each menu so as to set-up detailed function of the switch.

FIG. 19 illustrates an example of a screen displaying the customization of buttons of the operation device 3, by taking a customization of "2nd function" button for example. After the selection of each pull-down menu, by clicking "OK" on the second window, the second window disappears and the first windows comes back. Then by clicking the "Apply" on the first window, the new setting is fixed and activated, or by clicking the "CANCEL", the new selection is cancelled. Since a certain function is allocated to each button beforehand at factory, the user may restore the default by clicking "Restore Defaults" after the setting is customized once.

(Sixth Embodiment)

Referring to FIG. 19, an ultrasonic diagnostic apparatus and an operation device according to a sixth embodiment of the present invention will be described.

The operation device 3 of the embodiment is a modified and advanced type of the operation device 3 described in the above fifth embodiment, it is configured with an interface to change over the whole setting of buttons and/or the WFS scenario when booting up the ultrasonic diagnostic apparatus.

As described above, frequently used function of the ultrasonic diagnostic apparatus is different by a doctor, so is the WFS scenario. They are different not only by a doctor but also by a type of a tissue to be examined. Therefore, it is convenient for a user to select an appropriate WFS scenario in case of the WFS examination or a bundle of customized functions in case of the normal examination according to the doctor or the tissue.

By entering an ID number of each user when booting up the ultrasonic diagnostic apparatus, a WFS scenario or a bundle of functions customized aforetime for each user may start up. Or, it may be possible to apply a method that preparing several types of ready-made scenarios, or bundles of functions in advance, and appointing one of them which the user desires to use according to the doctor's preference or the type of the tissue to be examined when starting up the apparatus.

Figure 10:
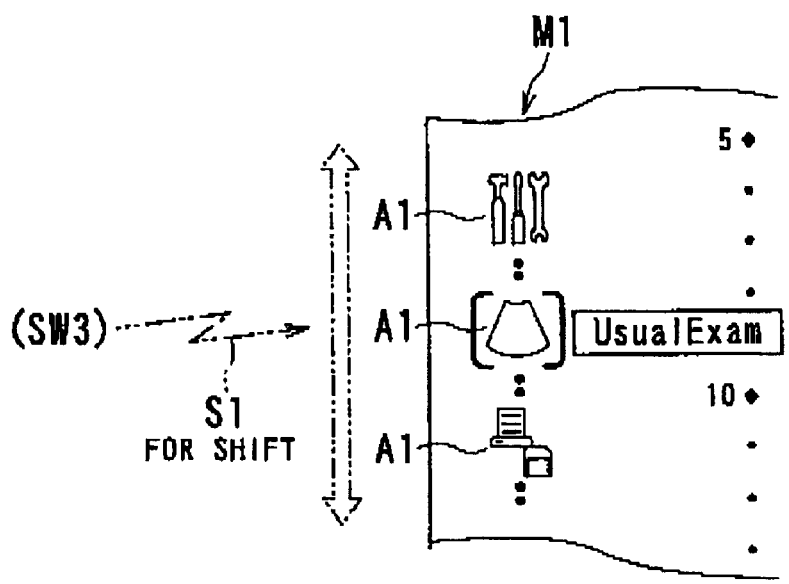
FIG. 10 is a view illustrating the selection of an activity on icon type WFS menu by operating the switch SW3 (shift button) of the operation device.
Figure 11:
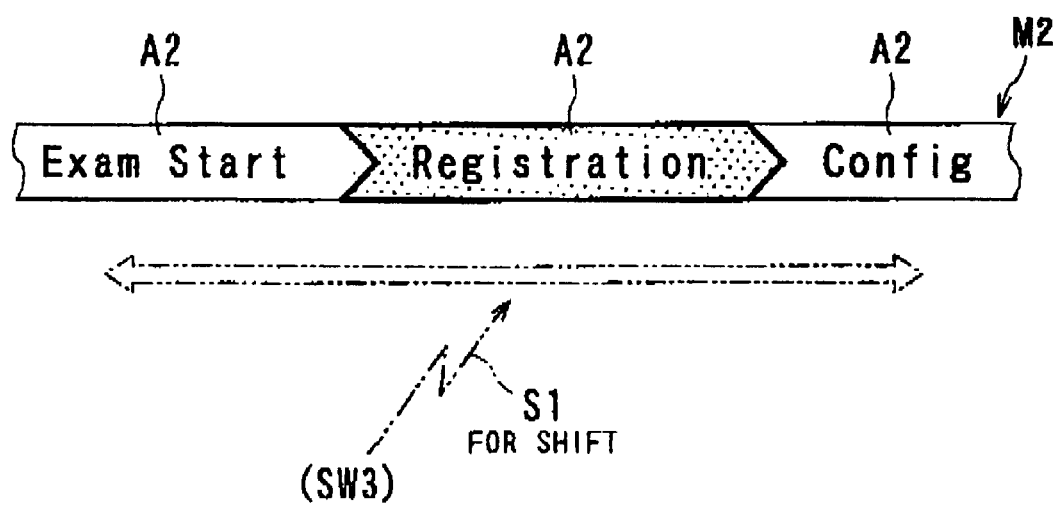
FIG. 11 is a view illustrating the selection of an activity on letter string type WFS menu by operating the switch SW3 (shift button) of the operation device.
Figure 12:
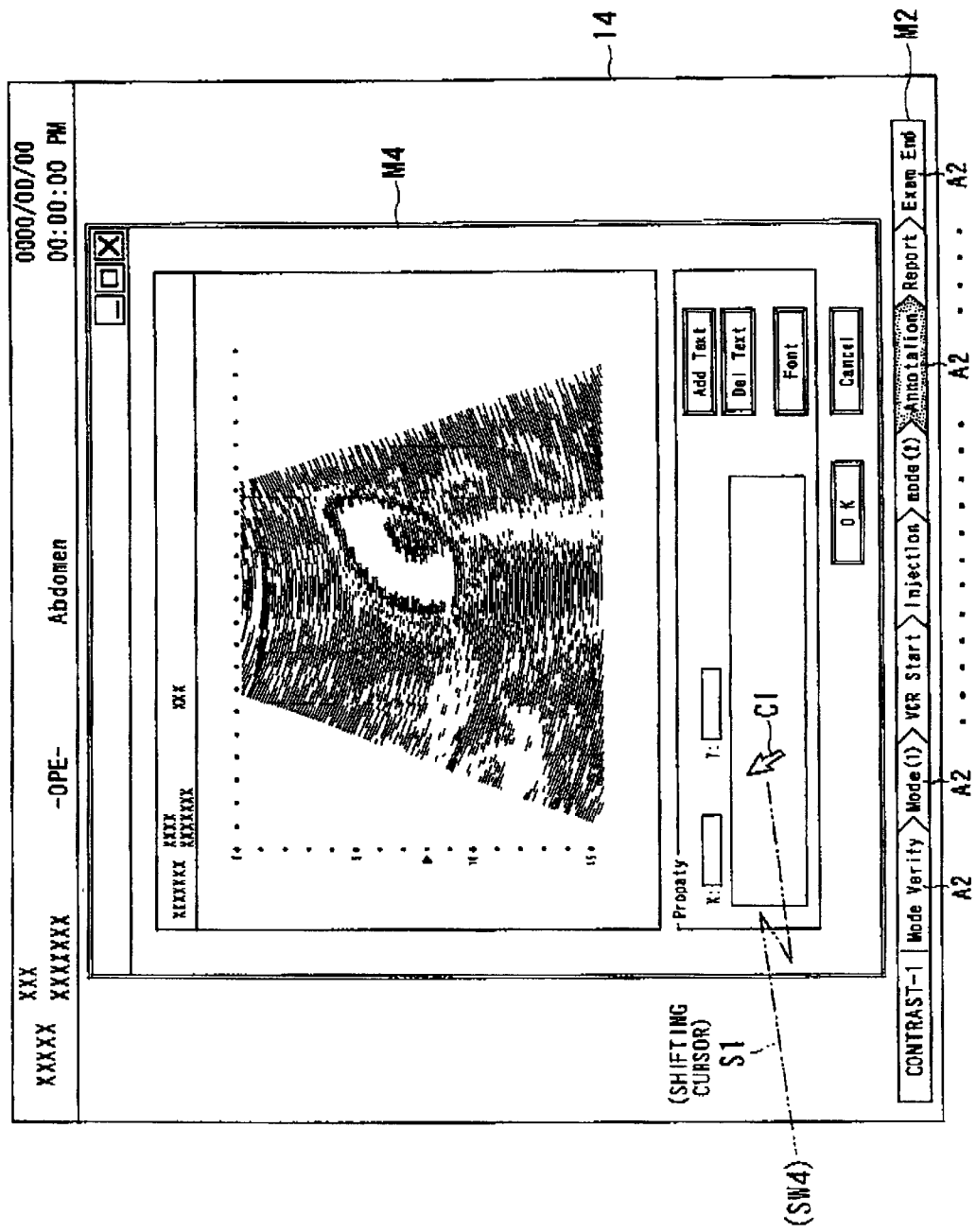
FIG. 12 is a view illustrating the shift of a cursor on measurement menu by operating the switch SW4 (shift button) of the operation device.

FIG. 10 illustrates an example of a screen on the monitor on the main frame 11, displaying the appointment of a scenario or a bundle of functions. Each scenario of the WFS or a bundle of functions is divided in accordance with a doctor's name and/or a type of tissue, and put into its own folder, and a tab, on which a folder name is written down, is attached to each folder. By clicking a tab with desired folder name, the contents of the folder is displayed on the screen in the form that a name of function is connected with the allocated button, so that a user may confirm the contents which is going to be used for the examination and select the most suitable scenario or a bundle of functions.

(Seventh Embodiment)

Figure 20:
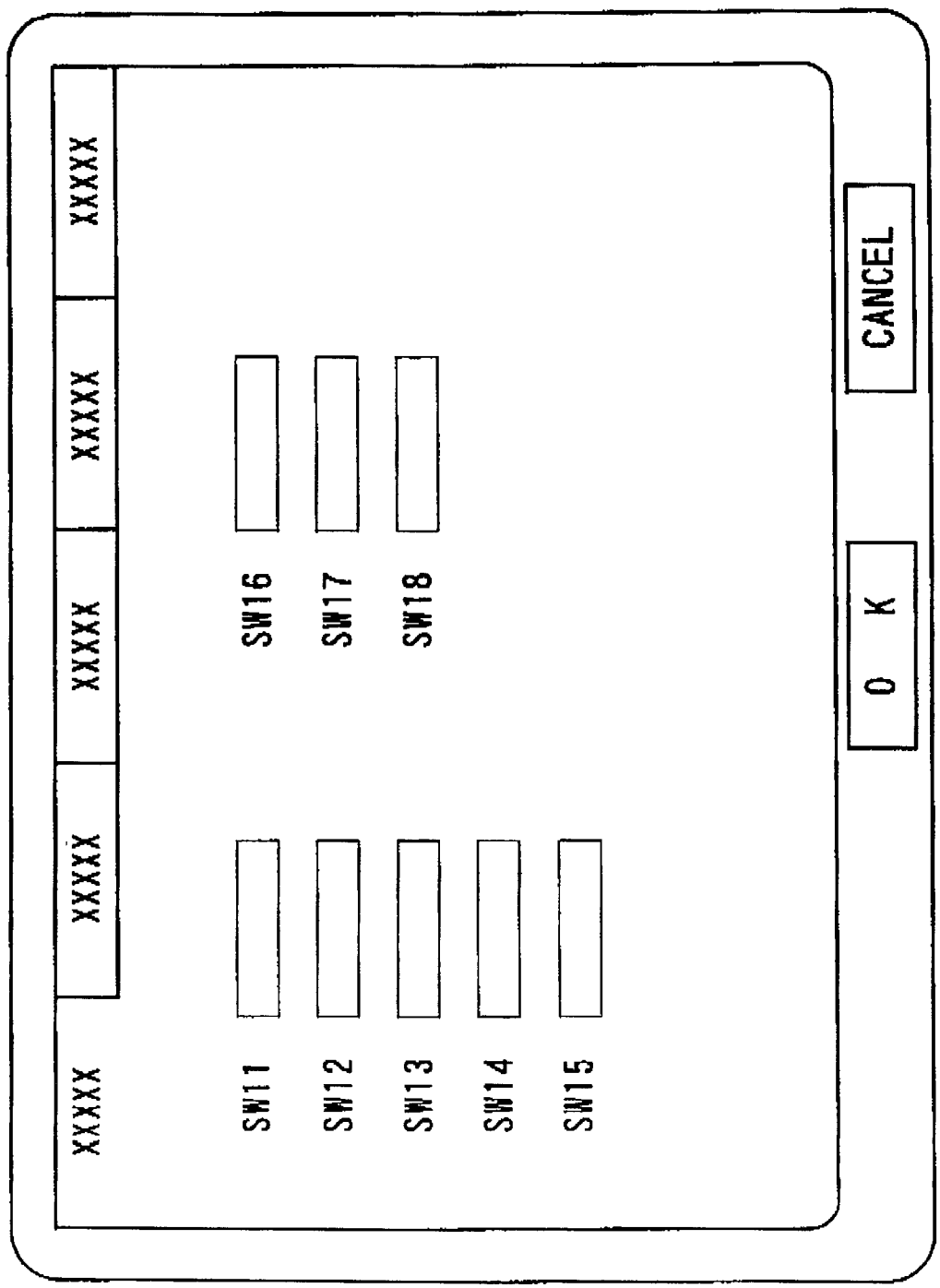
FIG. 20 illustrates an example of a screen on the monitor of the main frame, displaying the appointment of a scenario or a bundle of functions according to the sixth embodiment of the present invention.
Figure 21:
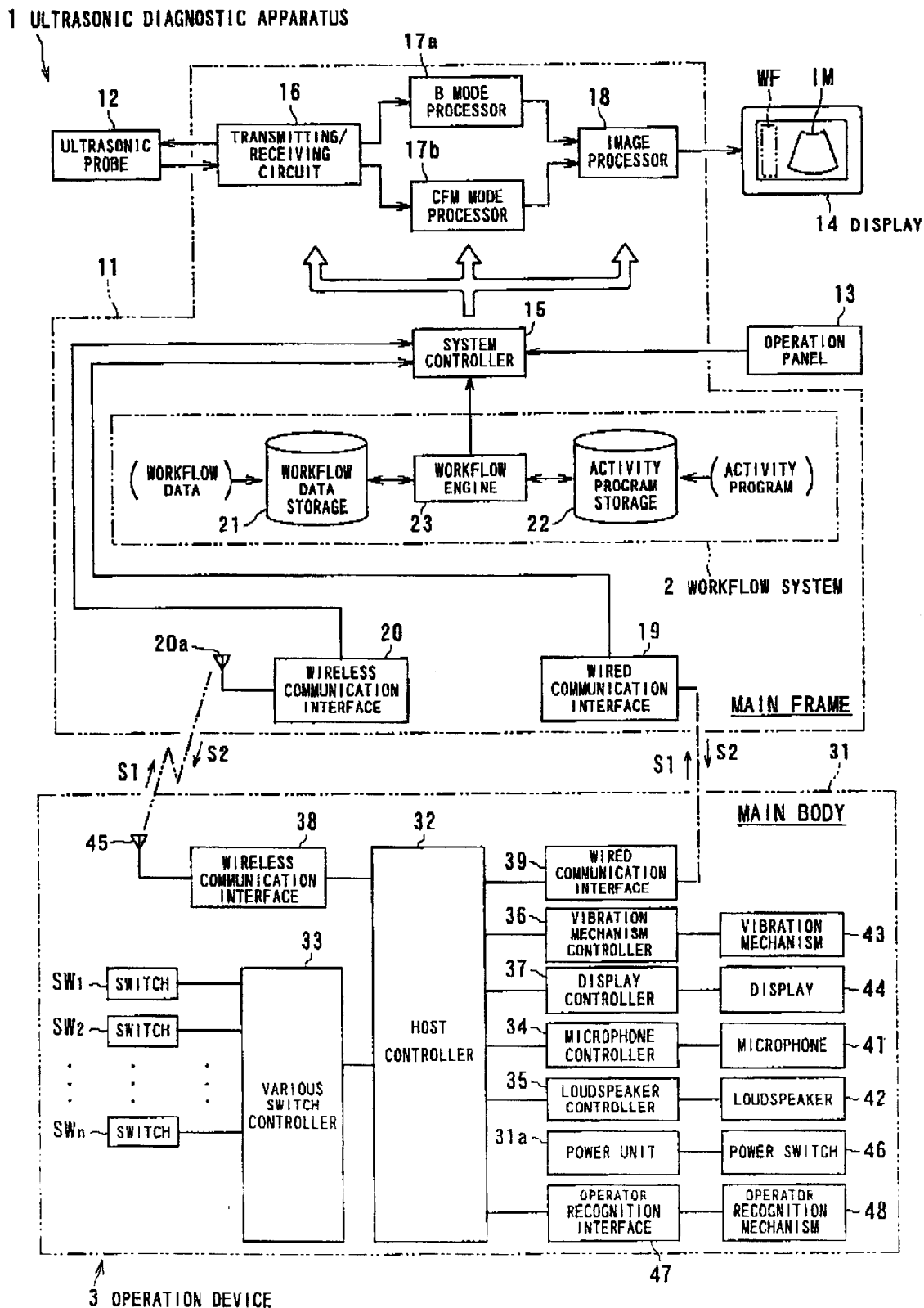
FIG. 21 is a schematic block diagram depicting an overall configuration of an ultrasonic diagnostic apparatus and its operation device according to the seventh embodiment of the present invention.

Referring to FIG. 20, an ultrasonic diagnostic apparatus and an operation device according to a seventh embodiment of the present invention will be described.

The operation device 3 of the embodiment is a further modified and advanced type of the operation device 3 described in the above fifth embodiment. It is configured with an interface to change over the whole setting of buttons and/or the WFS scenario when booting up the ultrasonic diagnostic apparatus as same as the operation device 3 of the sixth embodiment, however, the appointment of a scenario or a bundle of function is made by the operation of the operation device 3 of the embodiment, whereas it is made by the side of the main frame 11 in the sixth embodiment.

The operation device 3 is equipped with a function to recognize an operator such as a function of voice recognition, finger print recognition and retina recognition, so that the ultrasonic diagnostic apparatus 1 may recognize a doctor or a technician at the beginning of the examination through the intermediary of the operation device 3, and recall a suitable scenario or a bundle of function in the control of the doctor or the technician easily.

FIG. 20 is a schematic block diagram depicting an overall configuration of an ultrasonic diagnostic apparatus and its operation device of the embodiment of the present invention. This example is configured almost as same as that of the first embodiment but a mechanism 48 and an interface 47 for operator recognition is added.

Furthermore, as another applicable embodiment, giving a hardware ID to the operation device 3 is preferable so as to avoid interference which may occur when a plurality of the operation devices are used simultaneously.

The present invention is not limited to the described embodiments and modified examples which are typically shown, and various modifications and alterations can occur to one skilled in the art based on the claims without departing from the spirit of the invention. These modifications and alterations pertain to the claim(s) of the present invention.

What is claimed is:

1. An ultrasonic diagnostic apparatus comprising:
    a main frame configured to produce an ultrasonic image using a signal detected by an ultrasonic probe;
    an operation device configured to remote-control an operation of the main frame, and comprising a control command device which gives by an operation of an operator predetermined control commands specifying a function necessary for the operation of the main frame;
    a processing circuit configured to carry out processing necessary for obtaining the function; and
    a controller configured to switch the operation of the main frame by sequentially executing a plurality of execution items in accordance with the work procedure which predetermines an execution sequence of a plurality of execution items, and to select at least one of the plurality of the execution items when receiving a first control command given by the control command device and executes the selected execution item when receiving a second control command given by the control command device.

2. The ultrasonic diagnostic apparatus of claim 1, wherein the operation device is formed into a portable type of operation device.

3. The ultrasonic diagnostic apparatus of claim 2, wherein the operation device is formed into a detachable type of operation device.

4. The ultrasonic diagnostic apparatus of claim 2, wherein the operation device is configured to communicate by radio waves with the main frame.

5. The ultrasonic diagnostic apparatus of claim 2, wherein the function of the control command device is customized to the function frequently used in diagnosis with the ultrasonic diagnostic apparatus.

6. The ultrasonic diagnostic apparatus of claim 2, wherein the function of the control command device is allowed individually by each operator to be customized, stored, and recalled.

7. The ultrasonic diagnostic apparatus of claim 1, wherein the controller is configured to alter the execution sequence of the execution items in compliance with the operation of the operation device.

8. The ultrasonic diagnostic apparatus of claim 1, further comprising a generator configured to generate a display image by combining at least one of icons and letter strings which are allocated to the plurality of the execution items executed by the controller and ultrasonic image generated from the signals received by the ultrasonic probe.

9. The ultrasonic diagnostic apparatus of clam 8, wherein the generator comprises a changer configured to change the display status of at least one of the icons and the letter strings in order to visually grasp on the display at least one of the execution items selected by the operation of the shift button.

10. The ultrasonic diagnostic apparatus of claim 1, wherein:
the operation device further comprises a change-over button switching the operation concerning the work sequence and the operation concerning the main frame and is configured to communicate by radio waves with the main frame, and
the controller allocates at least one of switching functions set in the main frame to switches on the operation device so that the switching function may be executed by the operation device.

11. The ultrasonic diagnostic apparatus of claim 1, wherein the operation device comprises a plurality of buttons which are specialized to the selected functions.

12. The ultrasonic diagnostic apparatus of claim 11, wherein the selected functions comprises at least one of functions to freeze, to printout, and to store an ultrasonic image.

13. The ultrasonic diagnostic apparatus of claim 1, wherein:
the operation device further comprises a vibration mechanism having a driving circuit which works when a predetermined control command is received; and
the controller further comprises a communicator configured to give the control command to the operation device so that the vibration mechanism vibrates in case where at least one of predetermined conditions are met, the predetermined conditions including a change-over of a contrast echo mode set in the ultrasonic diagnostic apparatus, elapsing of an predetermined alarm time, and finding of an unusual electrocardiographic condition of a patient.

14. The ultrasonic diagnostic apparatus of claim 1 wherein:
the operation device further comprises a loudspeaker outputting voice when a predetermined control command is received; and
the controller further comprises a communicator configured to give the control command to the operation device so that the loudspeaker outputs voice in case where at least one of predetermined conditions are met, the predetermined conditions including a change-over of a contrast echo mode set in the ultrasonic diagnostic apparatus, elapsing of an predetermined alarm time, and finding of an unusual electrocardiographic condition of a patient.

15. The ultrasonic diagnostic apparatus of claim 1, wherein:
the operation device further comprises a microphone receiving voice including the operator's diagnostic observation; and
the controller further comprises a recorder configured to record the voice when the operator's diagnostic observation is provided.

16. The ultrasonic diagnostic apparatus of claim 1, wherein the control command device comprises a shift device outputting the first control command and an execution device outputting the second control command.

17. The ultrasonic diagnostic apparatus of claim 1, wherein the control command device comprises at least one of a push-type button, a trackball, a rotary dial, a rotary encoder and a voice recognizer.

18. An operation device for remote-controlling a main frame of an ultrasonic diagnostic apparatus producing an ultrasonic image using a signal detected by an ultrasonic probe by a controller configured to switch the operation of the main frame by sequentially executing a plurality of execution items in accordance with the work procedure which predetermines an execution sequence of a plurality of execution items, and to select at least one of the plurality of the execution items when receiving a first control command given by the control command device and executes the selected execution item when receiving a second control command given by the control command device comprising:
a control command device which gives by an operation of an operator predetermined control commands specifying a function necessary for the operation of the main frame to the controller; and
a processing circuit configured to carry out processing necessary for obtaining the function.

19. The operation device of claim 18, further comprising:
an LED display indicating both a residual quantity of a battery for power supply and a communication status with the main frame; and
the processing circuit executing necessary procedure to distinctively indicate at least one of a lack of the residual quantity of the battery, a waiting status and an established status of the communication.

20. The operation device of claim 18, further comprising:
a liquid crystal screen displaying at least a menu and present status of the operation of the operation device; and
the processing circuit executing a necessary procedure to display the present status of the operation of the operation device on the screen.

* * * * *